(12) United States Patent
Polezel

(10) Patent No.: US 7,045,154 B2
(45) Date of Patent: May 16, 2006

(54) USE OF FATS DERIVED FROM PALM TREES TO INCREASE DERMAL HYDRATION

(76) Inventor: Márcio Antonio Polezel, Rua José Oliveira Cassu, 447- Eden-Sorocaba, 18103-065, State of São Paulo (BR)

( * ) Notice: Subject to any disclaimer, the term of this patent is extended or adjusted under 35 U.S.C. 154(b) by 0 days.

(21) Appl. No.: 10/140,237

(22) Filed: May 7, 2002

(65) Prior Publication Data

US 2003/0147976 A1   Aug. 7, 2003

(30) Foreign Application Priority Data

Oct. 8, 2001   (BR)   .................... 0106625

(51) Int. Cl.
*A01K 35/78*   (2006.01)
(52) U.S. Cl. .................................... 424/725
(58) Field of Classification Search ............. 424/725, 424/195.1, 769, 776, 777, 401, 404, 484, 424/485; 510/108, 109, 130; 516/47; 422/129.1; 552/545

See application file for complete search history.

(56) References Cited

OTHER PUBLICATIONS

Hausman, M.; New Fats for the Soap Kettle; Soap (1937) vol. 13, nNo. 2, pp. 28-32, 37, 73.*
Campin; Guide to Plant Relationships; (Apr. 16, 1999), accessed from URL <www.ibiblio.org/ecolandtech/links/start-392001/msg00174.html> pp. 1-81.*

* cited by examiner

*Primary Examiner*—Patricia Leith
(74) *Attorney, Agent, or Firm*—Fish & Richardson P.C., P.A.

(57) ABSTRACT

The present invention relates to the use of natural or purified lipids or fats extracted from the fruit of a palm tree of the genus *Astrocaryum*, for increasing dermic and/or capillary hydration. The palm fats of the present invention may be used in hygiene products, cosmetics and pharmaceutical products. The invention also includes compositions containing the palm fats obtained according to the invention.

10 Claims, 2 Drawing Sheets

USE OF FATS DERIVED FROM PALM TREES TO INCREASE DERMAL HYDRATION

RELATED APPLICATIONS

This application claims priority to Brazilian patent application number PI0106625-0 filed Oct. 8, 2001, the entirety of which is incorporated herein by reference.

1. Field of the Invention

The present invention relates to the use of natural or purified and stable vegetable fat extracted from the fruit of the palm tree of the genus *Astrocaryum* for increasing dermal and/or capillary hydration/emollience, and compositions containing such fats. The material palm fats extracted according to the invention may be used in hygiene products, cosmetics and pharmaceutical products.

2. Background

Vegetable oils and fats usually have a hydrating/emollient action. Vegetable and animal fats and oils have long been known to be emollients (Berdick, 1972), as there are records of such use in cosmetics since 7000 B.C. (Denavarre, 1978). These lipidic compounds have a soothing effect on the skin and make the hair easier to comb. Vegetable oils and fats usually surpass animal oil and fats, keeping the advantage of being emollient, making the hair easier to comb, being safe and providing a soothing effect with less of a greasy feel (Berdick, 1972).

Emollients are substances that maintain skin's softness, smoothness and flexibility, having a protective effect against dehydration and irritation, forming a barrier that prevents the excessive loss of cutaneous moisture (Hamilton, 1971). In addition to these two known hydration, occlusion and humidifying mechanisms, a third mechanisms has been recently proposed, the intercellular lipids stabilization mechanism in the lamellar crystalline liquid phases. The fats and the oils or products that may act according to these mechanisms provide a longer lasting hydration (Barker, 1992).

Lipids commonly used in hydrating products may reduce the reaction of irritating agents in the skin (Loden and Anderson, 1996). The incorporation of these humidifying agents as topical use ingredients provides protection effects and substitution of some of the skin's lipidic layers (SCHAICH and KORTING, 1992).

The use of physiologic lipids lead to new forms of topical therapies for dermatoses (such as psoriasis, atopic dermatitis, and irritating dermatitis) caused by the abnormal functioning of the lipidic barrier (Feingold, et al., 1996).

SUMMARY OF THE INVENTION

The present invention comprises natural fats extracted from the fruits of a palm tree of the genus *Astrocaryum*, and their use in compositions and methods for increasing skin emolliance and/or hydration. The present invention is based on the surprising discovery that fats from *Astrocaryum* palm trees can increase in the skin's hydration potential up to ninety-four point eight percent (94.8%).

DETAILED DESCRIPTION

Figure 1:
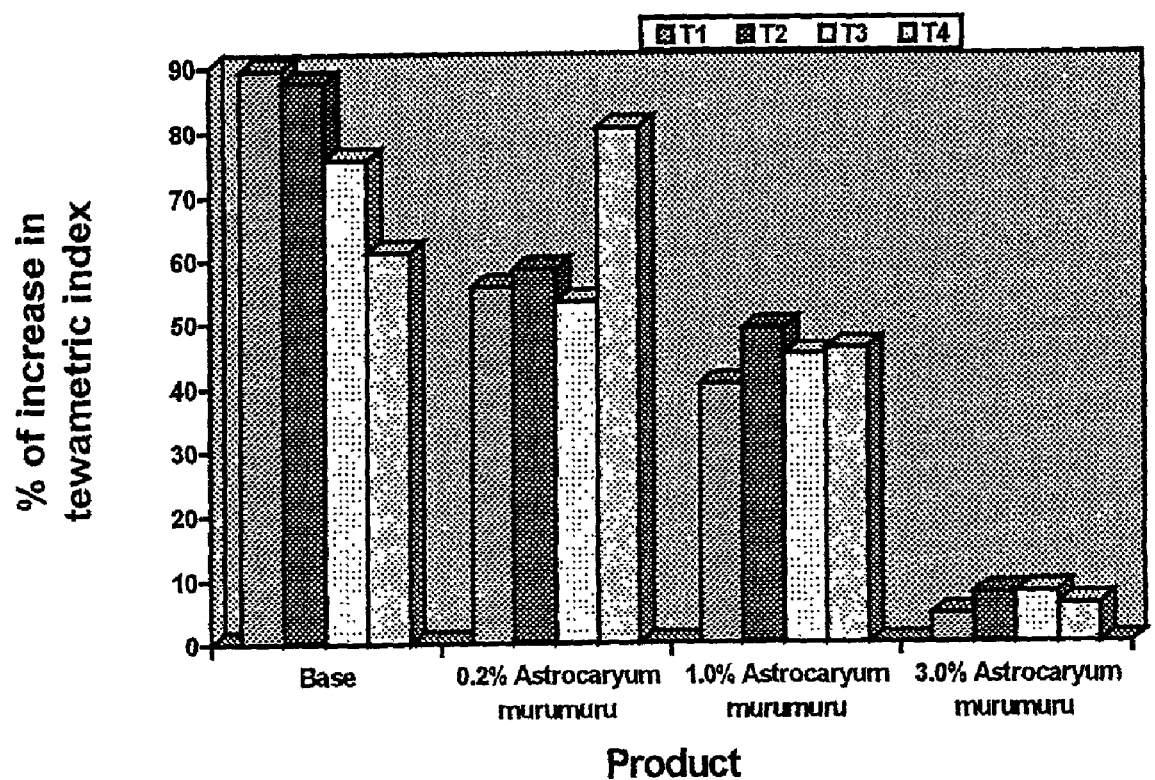
FIG. 1 is a graph illustrating the increase in the tewametric index using compositions of the present invention.

The fruits of the palm tree of the genus *Astrocaryum* have two parts—pulp and seeds—from which it is possible to obtain crude oils and fats by cold extraction, e.g., using hydraulic or continuous screw presses (expellers), or also by the traditional extraction method using boiling water and removing the oil or floating fat. The pulp may be processed dry or wet.

Crude fat from the fruit of the palm tree of the genus *Astrocaryum* can be obtained by cold pressing. The seed of the fruit is composed by a hard wooden shell and an inner almond that is removed after the shells are broken. The whole almond, either broken or ground, is subject to a cold extraction process in hydraulic or continuous screw presses (expellers), or further by the traditional extraction method using boiling water and removing the oil or floating fat, thus obtaining the crude fat. The crude fat then can be refined to obtain the fats of the present invention.

In a preferred embodiment, the crude fat from the fruit of the palm tree of the genus *Astrocaryum* is further refined according to the following process:

Step 1—De-gumming—if necessary, upon addition of two percent (2%) of water (70° C.) under the fat at 70° C.–80° C., agitating for 10–15 minutes, followed by centrifuging and removal of the heavy phase (gum).

Step 2—Neutralization—with NaOH aqueous solution, at 16–18° Be (Baumé), added to the oil at 70–80° C., agitating for 10–15 minutes, followed by centrifuging and removal of the heavy phase (sediments).

Step 3—Wash—with hot water (80–95° C.), two or three times, if necessary.

Step 4—Drying—under vacuum at 70–90° C.

Step 5—Bleaching—with bleaching clay (0.2–2%), under vacuum at 70–90° C. for 10–15 minutes, followed by filtering and cooling.

Step 6—Deodorization—under vacuum and $N_2$ current or water vapor at 120–180° C. for 1–5 hours, cool under vacuum to 45–50° C. and unload the reactor. Analyses: Acidity. Peroxide, color, stability.

Using the *Astrocaryum murumuru* and *Astrocaryum tucumã* species as an example, the typical physio-chemical and microbiologic characteristics of purified vegetable fat derived from *Astrocaryum* trees are as follows:

| Analyses | Unit | *Astrocaryum murumuru* | *Astrocaryum tucumã* |
|---|---|---|---|
| Appearance (25° C.) | — | Fatty solid | Fatty solid |
| Color | — | White to light yellow | White to light yellow |
| Odor | — | Characteristic | Characteristic |
| Acidity Index | mg KOH/g | 5.00 max. * | 5.00 max. * |
| Saponification Index | mg KOH/g | 200–270 * | 200–270 * |
| Iodine Index | g $I_2$/100 g | 24.0 max. * | 24.0 max. * |

-continued

| | °C. | | |
|---|---|---|---|
| Fusion Index | | | |
| Non-saponifiable materials | % p/p | 0.2 min. | 0.2 min. |
| Peroxides Index | mEq o2/1000 g | 12.0 max. | 12.0 max. |
| Water Content (KF) | % p/p | 0.30 max. | 0.30 max. |
| Standard Plate Count | UFC/ml | 100 max. | 100 max. |
| Fecal Coliform Count | UFC/ml | Absent | Absent |
| *Escherichia coli* | UFC/ml | Absent | Absent |
| Molds and Yeasts | UFC/ml | Absent | Absent |
| *Salmonella spp* | UFC/ml | Absent | Absent |
| *Staphylococcus aureus* | UFC/ml | Absent | Absent |
| *Pseudomonas sp* | UFC/ml | Absent | Absent |

\* Typical analysis

| Fatty Acids | % *Astrocaryum murumuru* | % *Astrocaryum tucumã* |
|---|---|---|
| C8:0 | 2.0 max. | 2.0 max. |
| C10:0 | 2.0 max. | 2.0 max. |
| C12:0 | 45–60 | 45–60 |
| C14:0 | 20–30 | 20–30 |
| C16:0 | 5.0–8.5 | 5.0–8.5 |
| C18:0 | 1.0–3.5 | 1.0–3.5 |
| C18:1 | 5.0–10.0 | 5.0–10.0 |
| C18:2 | 2.0–4.0 | 2.0–4.0 |

Fats derived from *Astrocaryum* trees comprise a combination of fatty acids, as exemplified in the table below. The fatty acids present in the highest concentration in the present purified vegetable fats of the genus *Astrocaryum* are lauric and myristic acids (medium-chain fatty acids).

Tests demonstrating the increase in hydration using the palm fats obtained as described above were carried out at EVIC Brasil, which is located at Av. Indianópolis, 1455—Planalto Paulista—04063-002—São Paulo. Tests for the evaluation of the Maintenance of the Cutaneous Barrier after a Single Application of a Cosmetic Product in Humans, considering the potential to obtain a cutaneous barrier forming and fully transcribed effect are described below.

PRODUCT STUDY/REFERENCE: EBb012b/01.034, 01.042, 01.043: EVALUATION OF THE MAINTENANCE OF THE CUTANEOUS BARRIER AFTER A SINGLE APPLICATION OF A COSMETIC PRODUCT IN HUMANS TEST PRODUCTS: Base Emulsion, 0.2%, 1% and 3% *Astrocaryum murumuru* emulsion The skin is an external barrier of our organism that performs several functions: protection against physical damage and ultraviolet radiation, control of the entrance of external materials (such as water and microorganisms), control of the excretion of fluids, salts and other substances, thermoregulation, among others.

Water is a very important component of skin for the maintenance of its physical integrity, elasticity and other properties.

The water in *stratum corneum* comes form inferior layers such as the epidermis and the dermis, and evaporates into the atmosphere.

The skin's water retention capacity may be evaluated in several ways. In this study the transepidermal water loss was determined in order to evaluate each hydrating product's efficacy and to improve the skin's hydric conditions after a single application.

The study evaluates the effect of a cosmetic product on the loss of the skin's transepidermal water loss after a single application (forearm) under controlled conditions.

The study was monocentric and was openly carried out. The control was intraindividual.

The study was carried out according to the general conditions of EVIC International and those that are specific from the Investigation Center and that were established for the performance of tests in humans.

| | Test product identification | | | |
|---|---|---|---|---|
| Name | 3% Creamy Emulsion *Astrocaryum murumuru* | 0.2% Creamy Emulsion *Astrocaryum murumuru* | 1% Creamy Emulsion *Astrocaryum murumuru* | Creamy Emulsion Vehicle |
| Reference | 01.034 | 01.041 | 01.042 | 01.043 |
| Batch # | CL028B01 | CL028E01 | CL028A01 | CL028D01 |
| Galenic Form and organoleptic characteristics | white emulsion | white emulsion | white emulsion | white emulsion |
| Necessary quantity / # of packages | 50 g/L | 50 g/L | 50 g/L | 50 g/L |

The formula for the products tested are described below.

Test Product Related Information

There were 10 volunteers whose data were extrapolated in the end of the study.

The specific inclusion criteria were as follows:
age: 18 to 54 years old
gender: male or female
phototype (Fitzpatrick): I to IV
dry and hairless skin in the front part of the forearm Specific Non-inclusive Criteria:

The specific non-inclusive criteria were as follows:
cutaneous marks in the experimental area, which may interfere with the evaluation of cutaneous reactions (pigmentation problems, scars, overdeveloped pilosity, ephelis, and neavi in large quantity, sun burn . . . )
allergy or reactivity to the category of the product tested
treatment using a hydrating product in the experimental zone 2 weeks before the beginning of the study
treatment using acidic Vitamin A and its derivatives within 3 months before the beginning of the study Experimental Areas The experimental areas are the front sides of the forearms: one randomly chosen forearm receives the product and the other serves as a non-treated control.

Product Application Conditions treated area: The product is applied once by the technician in charge of the study using a latex finger cots with a light finger massage up to penetration in an outlined area of 25 cm$^2$, at an amount of 2 mg/cm$^2$, in the institute.

control area: An area of 25 cm$^2$ is outlined in the contralateral forearm in the same manner as in the treated side, but no product is applied.

Conditions Required by the Study

The conditions imposed on the volunteers were as follows:
no other product different from the one being tested should be applied to the experimental area
no anti-allergic or anti-inflammatory treatment and/or with acidic vitamin A (and its derivatives) in the day of the study Instrumental Evaluation of the Hydrating Effect The hydration level of the skin's outer layers is quantitatively evaluated by the capacitance measures in different experimental periods.

The product's hydrating effect is evaluated by the hydration kinetic comparison gathered from two experimental areas.

All volunteers included in the study are considered in order to evaluate the test product's efficacy, so they are subject to all examinations in defined times.

Equipment

Transepidermic water loss (TEWL) is evaluated by a Tewameter TW210(Courage&Khazaka), which has a probe with a pair of sensors for temperature and humidity. According to Fick's Law, the diffusion of water (mass by area in a determined period) is proportional to the concentration gradient of water in the probe. There is a variation in the TEWL measured when the skin's hydration varies.

Environmental Condition

The environmental conditions imposed to the volunteers 30 minutes before the beginning of measurements, and throughout the whole test were:
Temperature: t°=20° C.+/−2° C.
Relative Humidity: RH=40%+/−15%

Measurement Sites

The instrumental measurements are performed in documented and defined sites of the control and treated areas.

Measurement Rate

The measures are taken before the product is applied, 1 hour (T1), 2 hours (T2), 3 hours (T3) and 4 hours (T4) after application of the product.

Evaluation Criteria

The system's transepidermic water loss amounts are expressed in g/m$^2$h. Expression and Interpretation of Results The individual results are expressed in:
absolute amounts in each experimental period,
variation rates in comparison with T0,
differences between the variation rates in comparison with T0 (control and treated areas).

The average and standard deviations are calculated.

The interpretation of the result is:
absolute, related to:
the percentage of "reactive" volunteers: volunteers in whose difference between variation rates in comparison with T0 (control and treated areas) is equal to or exceeds 10%,
the rate of increase in transepidermic water loss under when effect of the product: at each experimental period (difference between variation rates in comparison with T0—control and treated areas) in "reactive" volunteers,
rate of improvement in cutaneous barrier formation under when effect of the product: at each experimental period (normalized difference between the rate of increase in the tewametric index between the base and the product) in "reactive" volunteers.

Table 1 below sets out the typological characteristics of the volunteers tested.

Results

The individual data (absolute amounts for each experimental period, variation rates in comparison with T0, differences between variation rates in comparison with T0 of the control and treated areas) and the statistic analysis details are included in Table 2A–2D. The randomizing table of the left/right sides is included in Table 3.

"Reactive" volunteer results are shown below for each product:

| Formula 3 (01.034): 3.0% *Astrocaryum murumuru* | | | | |
|---|---|---|---|---|
| Variation of the tewametric indexes | Experimental periods | | | |
| compared with T0 | T1 | T2 | T3 | T4 |
| Treated area | 3.5 | 8.0 | 8.0 | 8.7 |
| Control area | −4.6 | −7.3 | −2.8 | 1.6 |

-continued

|  | | | | |
|---|---|---|---|---|
| Difference between the control and treated area | 4.7 | 7.8 | 8.0 | 6.1 |
| % of "reactive" volunteers | 60 | 60 | 70 | 70 |

| | |
|---|---|
| Maximum effect in the increase of TEWL in 3 hours | % of increase in tewametric index = 8.0 |
| Remaining effect 4 hours after application | % of increase in tewametric index = 6.1 |
| Maximum effect in the cutaneous barrier 1 hour after application | % of improvement in cutaneous barrier = 94.8 |

Formula 1 (01.041): 0.2% *Astrocaryum murumuru*

| Variation of the tewametric indexes compared with T0 | Experimental periods | | | |
|---|---|---|---|---|
| | T1 | T2 | T3 | T4 |
| Treated area | 51.5 | 51.8 | 50.9 | 70.9 |
| Control area | −4.3 | −6.7 | −2.5 | −9.5 |
| Difference between the control and treated area | 55.7 | 58.5 | 53.4 | 80.4 |
| % of "reactive" volunteers | 80 | 90 | 90 | 90 |

| | |
|---|---|
| Maximum effect in the increase of TEWL in 4 hours | % of increase in tewametric index = 80.4 |
| Remaining effect 4 hours after application | % of increase in tewametric index = 80.4 |
| Maximum effect in the cutaneous barrier 3 hours after application | % of improvement in cutaneous barrier = 29.3 |

Formula 2 (01.042): 1.0% *Astrocaryum murumuru*

| Variation of the tewametric indexes compared with T0 | Experimental periods | | | |
|---|---|---|---|---|
| | T1 | T2 | T3 | T4 |
| Treated area | 44.7 | 51.4 | 48.5 | 54.3 |
| Control area | 4.2 | 2.2 | 3.5 | 8.3 |
| Difference between the control and treated area | 40.5 | 49.2 | 45.0 | 46.0 |
| % of "reactive" volunteers | 90 | 80 | 70 | 80 |

| | |
|---|---|
| Maximum effect in the increase of TEWL in 2 hours | % of increase in tewametric index = 49.2 |
| Remaining effect 4 hours after application | % of increase in tewametric index = 46.0 |
| Maximum effect in the cutaneous barrier 1 hour after application | % of improvement in cutaneous barrier = 54.7 |

Formula 4 (01.043): Base Emulsion

| Variation of the tewametric indexes compared with T0 | Experimental periods | | | |
|---|---|---|---|---|
| | T1 | T2 | T3 | T4 |
| Treated area | 91.1 | 92.8 | 87.4 | 66.4 |
| Control area | 1.6 | 5.2 | 11.8 | 5.3 |
| Difference between the control and treated area | 89.5 | 87.6 | 75.6 | 61.1 |
| % of "reactive" volunteers | 100 | 100 | 100 | 90 |

| | |
|---|---|
| Maximum effect in the increase of TEWL in 4 hours | % of increase in tewametric index = 61.1 |
| Remaining effect 4 hours after application | % of increase in tewametric index = 61.1 |

FIG. 1 shows the % of increase in tewametric index

Figure 2:
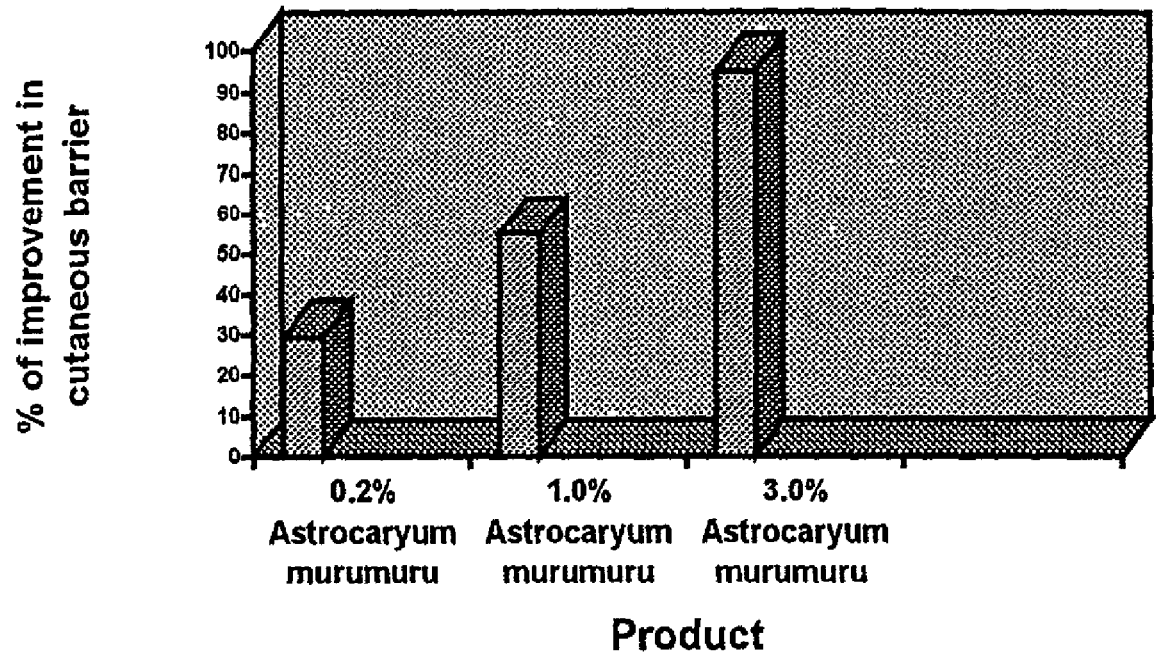
FIG. 2 is a graph illustrating the improvement in the cutaneous barrier using compositions of the present invention.

FIG. 2 shows the % of improvement in cutaneous barrier

Conclusions

Under the experimental conditions adopted and taking into consideration the evolution of the instrumental parameters considered:

the 0.2% *Astrocaryum murumuru* emulsion (Formula 1) has a 29.3% cutaneous barrier forming effect (in relation to the base) in 90% of the panel 3 hours after application, the 1.0% *Astrocaryum murumuru* emulsion (Formula 2) has a 54.7% cutaneous barrier forming effect (in relation to the base) in 90% of the panel 1 hour after application, the 3.0% *Astrocaryum murumuru* emulsion (Formula 3) has a 94.8% cutaneous barrier forming effect (in relation to the base) in 60% of the panel 1 hour after application.

TABLE 1

TYPOLOGICAL CHARACTERISTICS OF THE VOLUNTEERS

| Volunteers | | | Gender | | | |
|---|---|---|---|---|---|---|
| Ref. | Name Last name | Age | M = Male F = Female | Phototype* | Dry skin on forearm | Corneometric index on T0 |
| 1 | Tere C | 50 | F | III | X | 40 |
| 2 | Izab J | 51 | F | IV | X | 36 |
| 3 | Arad S | 40 | F | IV | X | 30 |
| 4 | Dolo N | 61 | F | IV | X | 28 |
| 5 | Patr F | 29 | F | IV | X | 44 |
| 6 | Simo F | 19 | F | III | X | 36 |
| 7 | Luiz M | 45 | F | IV | X | 27 |
| 8 | Luiz S | 45 | F | IV | X | 47 |
| 9 | Porf D | 45 | F | IV | X | 51 |
| 10 | Egla C | 39 | F | IV | X | 38 |

Key:
/ = no
X = yes
*Phototype according to Fitzpatrick's classification.

Fitzpatrick's classification

| Type | Hair | Skin | Freckles | Sun burns |
|---|---|---|---|---|
| I | red | light | +++ | Constant no tanning |
| II | light | light | ++ | Frequent tans lightly |
| III | light brown | light | + | Inconsistent tans moderately |
| IV | dark | brown | 0 | None considerable tanning |
| V | black and curly | black | 0 | 0 |

TABLE 2A.1

INSTRUMENTAL EVALUATION OF THE HYDRATING EFFECT
tewametric indexes
Product: 01.034 (Formula 3)

Control Area

| Volunteer's reference | Absolute Values | | | | | co V % Variation percentages in comparison with T0 | | | |
|---|---|---|---|---|---|---|---|---|---|
| | T0 | T1 | T2 | T3 | T4 | T1 | T2 | T3 | T4 |
| 1 | 1.5 | 1.0 | 1.0 | 1.3 | 1.5 | −33.3 | −33.3 | −13.3 | 0.0 |
| 2 | 1.4 | 1.2 | 1.2 | 1.3 | 1.0 | −14.3 | −14.3 | −7.1 | −28.6 |
| 3 | 1.0 | 1.0 | 1.0 | 1.0 | 1.3 | 0.0 | 0.0 | 0.0 | 30.0 |
| 4 | 4.5 | 4.5 | 4.6 | 4.6 | 4.6 | 0.0 | 2.2 | 2.2 | 2.2 |
| 5 | 4.4 | 4.8 | 4.5 | 4.8 | 4.6 | 9.1 | 2.3 | 9.1 | 4.5 |
| 6 | 4.8 | 5.2 | 5.0 | 5.1 | 5.3 | 8.3 | 4.2 | 6.3 | 10.4 |
| 7 | 1.8 | 2.1 | 1.9 | 2.0 | 1.9 | 16.7 | 5.6 | 11.1 | 5.6 |
| 8 | 7.5 | 8.0 | 7.9 | 7.5 | 7.4 | 6.7 | 5.3 | 0.0 | −1.3 |
| 9 | 2.6 | 2.8 | 2.6 | 2.3 | 2.3 | 7.7 | 0.0 | −11.5 | −11.5 |
| 10 | 3.1 | 2.8 | 2.8 | 3.0 | 3.3 | −9.7 | −9.7 | −3.2 | 6.5 |
| Vol. No. | 10 | 10 | 10 | 10 | 10 | 10 | 10 | 10 | 10 |
| Average | 3.3 | 3.3 | 3.3 | 3.3 | 3.3 | −0.9% | −3.8% | −0.7% | 1.8% |
| Standard Deviation | 2.0 | 2.3 | 2.2 | 2.1 | 2.1 | 14.7% | 12.3% | 8.3% | 15.1% |

TABLE 2A.2

| | Treated Area | | | | | | | | |
|---|---|---|---|---|---|---|---|---|---|
| | Absolute Values | | | | | tr V % Variation percentages in comparison with T0 | | | |
| Volunteer's reference | T1 | T1 | T2 | T3 | T4 | T1 | T2 | T3 | T4 |
| 1 | 1.2 | 2.2 | 2.4 | 2.0 | 2.2 | 83.3 | 100.0 | 66.7 | 83.3 |
| 2 | 0.6 | 0.6 | 0.7 | 1.1 | 1.0 | 0.0 | 16.7 | 83.3 | 66.7 |
| 3 | 2.5 | 1.6 | 1.5 | 0.5 | 0.5 | −36.0 | −40.0 | −80.0 | −80.0 |
| 4 | 4.0 | 5.0 | 5.0 | 4.2 | 4.3 | 25.0 | 25.0 | 5.0 | 7.5 |
| 5 | 3.6 | 4.1 | 4.0 | 4.5 | 4.8 | 13.9 | 11.1 | 25.0 | 33.3 |
| 6 | 4.8 | 4.5 | 4.5 | 4.5 | 4.6 | −6.3 | −6.3 | −6.3 | −4.2 |
| 7 | 1.5 | 1.7 | 1.8 | 1.9 | 1.5 | 13.3 | 20.0 | 26.7 | 0.0 |
| 8 | 7.0 | 6.8 | 7.0 | 6.5 | 6.1 | −2.9 | 0.0 | −7.1 | −12.7 |
| 9 | 4.7 | 3.4 | 3.5 | 3.5 | 3.5 | −27.7 | −25.5 | −25.5 | −25.5 |
| 10 | 4.1 | 3.0 | 3.1 | 3.2 | 3.3 | −26.8 | −24.4 | −22.0 | −19.5 |
| Vol. No. | 10 | 10 | 10 | 10 | 10 | 10 | 10 | 10 | 10 |
| Average | 3.4 | 3.3 | 3.4 | 3.2 | 3.2 | 3.6% | 7.7% | 6.6% | 4.9% |
| Standard Deviation | 2.0 | 1.9 | 1.9 | 1.8 | 1.8 | 34.4% | 39.1% | 47.1% | 47.1% |

INSTRUMENTAL EVALUATION OF THE HYDRATING EFFECT
tewametric indexes
Product: 01.034 (Formula 3)
Table 2A.3

| Volunteer's reference | tr V − co V difference (%) | | | | Reactive volunteers* |
|---|---|---|---|---|---|
| | T1 | T2 | T3 | T4 | |
| 1 | 116.7 | 133.3 | 80.0 | 83.3 | X |
| 2 | 14.3 | 31.0 | 90.5 | 95.2 | X |
| 3 | −36.0 | −40.0 | −80.0 | −110.0 | X |
| 4 | 25.0 | 22.8 | 2.8 | 5.3 | / |
| 5 | 4.8 | 8.8 | 15.9 | 28.8 | X |
| 6 | −14.6 | −10.4 | −12.5 | −14.6 | X |
| 7 | −3.3 | 14.4 | 15.6 | −5.6 | / |
| 8 | −9.5 | −5.3 | −7.1 | −11.4 | / |
| 9 | −35.4 | −25.5 | −14.0 | −14.0 | X |
| 10 | −17.2 | −14.7 | −18.7 | −26.0 | X |

Key:
/ = no
X = yes
*volunteers whose difference between the variation percentage in comparison to T0 of treated and control areas is equal to or above 10%

TABLE 2B

INSTRUMENTAL EVALUATION OF THE HYDRATING EFFECT
tewametric indexes
Product: 01.041 (Formula 1)
Table 2B.1

| | Control Area | | | | | | | | |
|---|---|---|---|---|---|---|---|---|---|
| | Absolute Values | | | | | co V % Variation percentages in comparison with T0 | | | |
| Volunteer's reference | T0 | T1 | T2 | T3 | T4 | T1 | T2 | T3 | T4 |
| 1 | 1.1 | 0.9 | 0.8 | 1.2 | 1.0 | −18.2 | −27.3 | 9.1 | −9.1 |
| 2 | 1.2 | 1.2 | 1.1 | 1.2 | 0.8 | 0.0 | −8.3 | 0.0 | −33.3 |
| 3 | 0.6 | 0.8 | 0.8 | 0.8 | 0.7 | 33.3 | 33.3 | 33.3 | 16.7 |
| 4 | 4.3 | 4.3 | 4.3 | 4.5 | 4.3 | 0.0 | 0.0 | 4.7 | 0.0 |
| 5 | 4.4 | 4.1 | 4.1 | 4.4 | 4.1 | −6.8 | −6.8 | 0.0 | −6.8 |

TABLE 2B-continued

INSTRUMENTAL EVALUATION OF THE HYDRATING EFFECT
tewametric indexes
Product: 01.041 (Formula 1)
Table 2B.1

Control Area

| Volunteer's reference | Absolute Values | | | | | co V % Variation percentages in comparison with T0 | | | |
|---|---|---|---|---|---|---|---|---|---|
| | T0 | T1 | T2 | T3 | T4 | T1 | T2 | T3 | T4 |
| 6 | 4.0 | 4.3 | 4.0 | 4.0 | 4.4 | 7.5 | 0.0 | 0.0 | 10.0 |
| 7 | 1.6 | 1.3 | 1.3 | 1.1 | 1.0 | −18.8 | −18.8 | −37.5 | −37.5 |
| 8 | 6.7 | 6.5 | 7.0 | 6.8 | 6.1 | −3.0 | 4.5 | 1.5 | −9.0 |
| 9 | 2.5 | 2.0 | 2.0 | 2.1 | 2.2 | −20.0 | −20.0 | −16.0 | −12.0 |
| 10 | 2.4 | 2.1 | 2.0 | 2.1 | 2.3 | −12.5 | −16.7 | −12.5 | −4.2 |
| Vol. No. | 10 | 10 | 10 | 10 | 10 | 10 | 10 | 10 | 10 |
| Average | 2.9 | 2.8 | 2.7 | 2.8 | 2.7 | −3.8% | −6.0% | −1.7% | −8.5% |
| Standard Deviation | 1.9 | 1.9 | 2.0 | 2.0 | 1.9 | 16.0% | 17.2% | 18.3% | 16.8% |

TABLE 2B.2

Treated Area

| Volunteer's reference | Absolute Values | | | | | tr V % Variation percentages in comparison with T0 | | | |
|---|---|---|---|---|---|---|---|---|---|
| | T1 | T1 | T2 | T3 | T4 | T1 | T2 | T3 | T4 |
| 1 | 0.4 | 0.7 | 0.6 | 0.6 | 1.0 | 75.0 | 50.0 | 50.0 | 150.0 |
| 2 | 0.4 | 0.5 | 0.7 | 0.6 | 1.0 | 25.0 | 75.0 | 50.0 | 150.0 |
| 3 | 1.8 | 1.1 | 0.9 | 0.5 | 0.4 | −38.9 | −50.0 | −72.2 | −77.8 |
| 4 | 4.2 | 3.8 | 3.9 | 4.0 | 3.9 | −9.5 | −7.1 | −4.8 | −7.1 |
| 5 | 1.3 | 2.4 | 2.3 | 2.5 | 2.6 | 84.6 | 76.9 | 92.3 | 100.0 |
| 6 | 3.3 | 3.5 | 4.3 | 4.7 | 4.5 | 6.1 | 30.3 | 42.4 | 36.4 |
| 7 | 1.4 | 2.0 | 1.9 | 1.8 | 1.8 | 42.9 | 35.7 | 28.6 | 28.6 |
| 8 | 2.3 | 5.1 | 4.8 | 5.0 | 4.5 | 121.7 | 108.7 | 117.4 | 95.7 |
| 9 | 1.8 | 3.0 | 3.0 | 3.3 | 2.8 | 66.7 | 66.7 | 83.3 | 55.6 |
| 10 | 1.5 | 2.7 | 2.6 | 2.5 | 3.0 | 80.0 | 73.3 | 66.7 | 100.0 |
| Vol. No. | 10 | 10 | 10 | 10 | 10 | 10 | 10 | 10 | 10 |
| Average | 1.8 | 2.5 | 2.5 | 2.6 | 2.6 | 45.4% | 45.9% | 45.4% | 63.1% |
| Standard Deviation | 1.2 | 1.5 | 1.5 | 1.7 | 1.5 | 49.4% | 49.4% | 53.7% | 71.2% |

INSTRUMENTAL EVALUATION OF THE HYDRATING EFFECT
tewametric indexes
Product: 01.041
Table 2B.3

| Volunteer's reference | tr V 0 co V difference (%) | | | | Reactive volunteers* |
|---|---|---|---|---|---|
| | T1 | T2 | T3 | T4 | |
| 1 | 93.2 | 77.3 | 40.9 | 159.1 | X |
| 2 | 25.0 | 83.3 | 50.0 | 183.3 | X |
| 3 | −72.2 | −83.3 | −105.6 | −94.4 | X |
| 4 | −9.5 | −7.1 | −9.4 | −7.1 | / |
| 5 | 91.4 | 83.7 | 92.3 | 106.8 | X |
| 6 | −1.4 | 30.3 | 42.4 | 26.4 | X |
| 7 | 61.6 | 54.5 | 66.1 | 66.1 | X |
| 8 | 124.7 | 104.2 | 115.9 | 104.6 | X |
| 9 | 86.7 | 86.7 | 99.3 | 67.6 | X |
| 10 | 92.5 | 90.0 | 79.2 | 104.2 | X |

Key:
/ = no
X = yes
*volunteers whose difference between the variation percentage in comparison to T0 of treated and control areas is equal to or above 10%

TABLE 2C

INSTRUMENTAL EVALUATION OF THE HYDRATING EFFECT
tewametric indexes
Product 01.042 (Formula 2)

Table 2C.1

Control Area

| Volunteer's reference | Absolute Values | | | | | co V % Variation percentages in comparison with T0 | | | |
|---|---|---|---|---|---|---|---|---|---|
| | T1 | T1 | T2 | T3 | T4 | T1 | T2 | T3 | T4 |
| 1 | 1.6 | 1.7 | 1.8 | 1.5 | 2.0 | 6.3 | 12.5 | −6.3 | 25.0 |
| 2 | 2.0 | 2.1 | 2.0 | 2.0 | 1.8 | 5.0 | 0.0 | 0.0 | −10.0 |
| 3 | 1.4 | 1.5 | 1.5 | 1.0 | 1.5 | 7.1 | 7.1 | −28.6 | 7.1 |
| 4 | 4.6 | 4.0 | 4.5 | 4.5 | 4.6 | −13.0 | −2.2 | −2.2 | 0.0 |
| 5 | 2.6 | 2.3 | 2.5 | 2.8 | 2.8 | −11.5 | −2.3 | 7.7 | 7.7 |
| 6 | 4.4 | 4.1 | 4.5 | 4.4 | 4.4 | −6.8 | 2.3 | 0.0 | 0.0 |
| 7 | 1.3 | 1.6 | 1.1 | 1.6 | 1.6 | 23.1 | −15.4 | 23.1 | 23.1 |
| 8 | 4.1 | 4.7 | 4.5 | 3.9 | 4.2 | 14.6 | 9.8 | −4.9 | 2.4 |
| 9 | 2.5 | 2.3 | 2.0 | 2.4 | 2.7 | −8.0 | −20.0 | −4.0 | 8.0 |
| 10 | 2.0 | 2.5 | 2.6 | 3.0 | 2.4 | 25.0 | 30.0 | 50.0 | 20.0 |
| Vol. No. | 10 | 10 | 10 | 10 | 10 | 10 | 10 | 10 | 10 |
| Average | 2.7 | 2.7 | 2.7 | 2.7 | 2.8 | 4.2% | 2.2% | 3.5% | 8.3% |
| Standard Deviation | 1.3 | 1.2 | 1.3 | 1.2 | 1.2 | 13.9% | 14.2% | 20.7% | 11.3% |

TABLE 2C.2

Treated Area

| Volunteer's reference | Absolute Values | | | | | tr V % Variation percentages in comparison with T0 | | | |
|---|---|---|---|---|---|---|---|---|---|
| | T0 | T1 | T2 | T3 | T4 | T1 | T2 | T3 | T4 |
| 1 | 1.1 | 1.1 | 1.4 | 1.8 | 1.8 | 0.0 | 27.3 | 63.6 | 63.6 |
| 2 | 0.4 | 1.7 | 1.4 | 1.4 | 1.6 | 325.0 | 250.0 | 250.0 | 300.0 |
| 3 | 1.2 | 1.0 | 1.3 | 1.3 | 1.5 | −16.7 | 8.3 | 8.3 | 25.0 |
| 4 | 3.2 | 3.8 | 4.6 | 4.0 | 3.8 | 18.8 | 43.8 | 25.0 | 18.8 |
| 5 | 2.8 | 3.2 | 3.8 | 4.1 | 3.7 | 14.3 | 35.7 | 46.4 | 32.1 |
| 6 | 3.4 | 4.1 | 5.0 | 4.4 | 3.8 | 20.6 | 47.1 | 29.4 | 11.8 |
| 7 | 1.2 | 1.6 | 1.8 | 1.5 | 1.5 | 33.3 | 50.0 | 25.0 | 25.0 |
| 8 | 8.0 | 7.8 | 8.0 | 7.3 | 7.1 | −2.5 | 0.0 | −8.8 | −11.3 |
| 9 | 2.5 | 2.6 | 2.8 | 2.4 | 2.7 | 4.0 | 12.0 | −4.0 | 8.0 |
| 10 | 2.0 | 3.0 | 2.8 | 3.0 | 3.4 | 50.0 | 40.0 | 50.0 | 70.0 |
| Vol. No. | 10 | 10 | 10 | 10 | 10 | 10 | 10 | 10 | 10 |
| Average | 2.6 | 3.0 | 3.3 | 3.1 | 3.1 | 44.7% | 51.4% | 48.5% | 54.3% |
| Standard Deviation | 2.1 | 2.0 | 2.1 | 1.9 | 1.7 | 100.3% | 71.8% | 74.5% | 89.7% |

INSTRUMENTAL EVALUATION OF THE HYDRATING EFFECT
tewametric indexes
Product: 01.042

Table 2C.3

| Volunteer's reference | tr V 0 co V difference (%) | | | | Reactive volunteers* |
|---|---|---|---|---|---|
| | T1 | T2 | T3 | T4 | |
| 1 | −6.3 | 14.8 | 69.9 | 38.6 | X |
| 2 | 320.0 | 250.0 | 250.00 | 310.00 | X |
| 3 | −23.8 | 1.2 | 36.9 | 17.9 | X |
| 4 | 31.8 | 45.9 | 27.2 | 18.8 | X |
| 5 | 25.8 | 38.0 | 38.7 | 24.5 | X |
| 6 | 27.4 | 44.8 | 29.4 | 11.8 | X |
| 7 | 10.3 | 65.4 | 1.9 | 1.9 | X |
| 8 | −17.1 | −9.8 | −3.9 | −13.7 | X |
| 9 | 12.0 | 32.0 | 0.0 | 0.0 | X |
| 10 | 25.0 | 10.0 | 0.0 | 50.0 | X |

Key:
/ = no
X = yes
*volunteers whose difference between the variation percentage in comparison to T0 of treated and control areas is equal to or above 10%

TABLE 2D

INSTRUMENTAL EVALUATION OF THE HYDRATING EFFECT
tewametric indexes
Product 01.043 (Formula 4)

Table 2D.1

| | | | | | | Control Area | | | |
|---|---|---|---|---|---|---|---|---|---|
| Volunteer's | Absolute Values | | | | | co V %<br>Variation percentages in<br>comparison with T0 | | | |
| reference | T0 | T1 | T2 | T3 | T4 | T1 | T2 | T3 | T4 |
| 1 | 1.2 | 1.2 | 1.5 | 1.5 | 1.7 | 0.0 | 28.3 | 25.0 | 41.7 |
| 2 | 2.1 | 2.0 | 2.1 | 2.5 | 2.0 | −4.8 | 0.0 | 19.0 | −4.8 |
| 3 | 2.5 | 2.3 | 2.3 | 2.0 | 1.9 | −8.0 | −8.0 | −20.0 | −24.0 |
| 4 | 4.5 | 4.6 | 5.0 | 5.5 | 4.8 | 2.2 | 11.1 | 22.2 | 6.7 |
| 5 | 2.1 | 2.6 | 2.6 | 2.8 | 2.6 | 23.8 | 23.8 | 33.3 | 23.8 |
| 6 | 5.0 | 5.1 | 5.0 | 5.4 | 5.3 | 2.0 | 0.0 | 8.0 | 6.0 |
| 7 | 2.0 | 2.1 | 1.8 | 2.2 | 2.0 | 5.0 | −10.0 | 10.0 | 0.0 |
| 8 | 8.0 | 7.5 | 7.8 | 8.7 | 8.2 | −6.3 | −2.5 | 8.7 | 2.5 |
| 9 | 4.2 | 4.0 | 4.0 | 3.5 | 3.8 | −4.8 | −4.8 | −16.7 | −9.5 |
| 10 | 2.8 | 3.0 | 3.2 | 3.6 | 3.1 | 7.1 | 14.3 | 28.6 | 10.7 |
| Vol. No. | 10 | 10 | 10 | 10 | 10 | 10 | 10 | 10 | 10 |
| Average | 3.4 | 3.4 | 3.5 | 3.8 | 3.5 | 1.6% | 5.2% | 11.8% | 5.3% |
| Standard Deviation | 2.0 | 1.9 | 2.0 | 2.2 | 2.1 | 9.3% | 13.4% | 18.0% | 18.0% |

TABLE 2D.2

| | | | | | | Treated Area | | | |
|---|---|---|---|---|---|---|---|---|---|
| Volunteer's | Absolute Values | | | | | tr V %<br>Variation percentages in comparison<br>with T0 | | | |
| reference | T0 | T1 | T2 | T3 | T4 | T1 | T2 | T3 | T4 |
| 1 | 0.8 | 2.5 | 2.0 | 2.0 | 2.0 | 212.5 | 150.0 | 150.0 | 150.0 |
| 2 | 0.3 | 2.1 | 2.1 | 2.0 | 1.5 | 600.0 | 600.0 | 566.7 | 400.0 |
| 3 | 0.8 | 1.0 | 1.0 | 1.3 | 0.8 | 25.0 | 25.0 | 62.5 | 0.0 |
| 4 | 2.5 | 4.0 | 4.3 | 4.3 | 4.3 | 60.0 | 72.0 | 72.0 | 72.0 |
| 5 | 5.1 | 4.1 | 4.3 | 4.3 | 4.0 | −19.6 | −15.7 | −15.7 | −21.6 |
| 6 | 2.0 | 4.3 | 5.1 | 4.5 | 4.7 | 115.0 | 155.0 | 125.0 | 135.0 |
| 7 | 1.4 | 1.2 | 1.6 | 1.3 | 1.4 | −14.3 | 14.3 | −7.1 | 0.0 |
| 8 | 13.6 | 10.0 | 10.0 | 9.2 | 9.2 | −26.5 | −26.5 | −32.4 | −32.4 |
| 9 | 5.9 | 4.0 | 3.8 | 4.0 | 4.0 | −32.2 | −35.6 | −32.2 | −32.2 |
| 10 | 4.7 | 4.3 | 4.2 | 4.0 | 4.4 | −8.5 | −10.6 | −14.9 | −6.4 |
| Vol. No. | 10 | 10 | 10 | 10 | 10 | 10 | 10 | 10 | 10 |
| Average | 3.7 | 3.8 | 3.8 | 3.7 | 3.6 | 91.1% | 92.8% | 87.4% | 66.4% |
| Standard Deviation | 4.0 | 2.5 | 2.6 | 2.3 | 2.4 | 194.9% | 191.1% | 180.9% | 135.1% |

INSTRUMENTAL EVALUATION OF THE HYDRATING EFFECT
tewametric indexes
Product: 01.043

Table 2D.3

| Volunteer's | tr V 0 co V difference (%) | | | | Reactive |
|---|---|---|---|---|---|
| reference | T1 | T2 | T3 | T4 | volunteers* |
| 1 | 212.5 | 121.7 | 125.0 | 108.3 | X |
| 2 | 604.8 | 600.0 | 547.6 | 404.8 | X |
| 3 | 33.0 | 33.0 | 82.5 | 24.0 | X |
| 4 | 57.8 | 60.9 | 49.8 | 65.3 | X |
| 5 | −43.4 | −39.5 | −49.0 | −45.4 | X |
| 6 | 113.0 | 155.0 | 117.0 | 129.0 | X |
| 7 | −19.3 | 24.3 | −17.1 | 0.0 | X |
| 8 | −20.2 | −24.0 | −41.1 | −34.9 | X |
| 9 | −27.4 | −30.8 | −15.5 | −22.7 | X |
| 10 | −15.7 | −24.9 | 043.5 | −17.1 | X |

Key:
/ = no
X = yes
*volunteers whose difference between the variation percentage in comparison to T0 of treated and control areas is equal to or above 10%

TABLE 3

INSTRUMENTAL EVALUATION OF THE HYDRATING EFFECT
Randomizing Table

| Ref. | 01.034 | | 01.041 | | 01.042 | | 01.043 | |
|---|---|---|---|---|---|---|---|---|
| Vol. | Treated | Control | Treated | Control | Treated | Control | Treated | Control |
| 1 | R | L | R | L | L | R | L | R |
| 2 | R | L | R | L | L | R | L | R |
| 3 | L | R | L | R | R | L | R | L |
| 4 | R | L | R | L | L | R | L | R |
| 5 | L | R | L | R | R | L | R | L |
| 6 | L | R | L | R | R | L | R | L |
| 7 | R | L | R | L | L | R | L | R |
| 8 | L | R | L | R | R | L | R | L |
| 9 | L | R | L | R | R | L | R | L |
| 10 | L | R | L | R | R | L | R | L |

Key: D
R = right forearm
L = left forearm

FORMULAS

Formula 1: Reference 01.041

0.2% *Astrocaryum murumuru* Creamy Emulsion

Phase A (%pp)

Non-ionic self-emulsifying base 5.00
Keto-stearic alcohol 2.00
Lanolin Alcohol, mineral oil 2.00
Cetyl Acetate, acetylated lanolin alcohol 2.00
Murumuru butter 0.20
Butyparabene, Ethylparabene, Methylparabene, Phenoxyethanol, Proplyparabene 0.50

Phase B

Distilled water qsp 100.00
Disodium edetate 99.3%

Formula 2: Reference 01.042

1% *Astrocaryum murumuru* Creamy Emulsion

Phase A (%pp)

Non-ionic self-emulsifying base 5.00
Keto-stearic alcohol 2.00
Lanolin, Alcohol, mineral oil 2.00
Cetyl Acetate, acetylated lanoliun alcohol 2.00
Murumuru butter 0.50
butyparabene, Ethyparabene, Methylparabene, Propylparabene 0.50

Phase B

Distilled water qsp 100.00
Dosodium edate 99.3%

Formula 3: Reference 01.034

3% *Astrocaryum murumuru* Creamy Emulsion

| | (% pp) |
|---|---|
| PHASE A | |
| Non-ionic self-emulsifying base | 5.00 |
| Keto-stearic alcohol | 2.00 |
| Lanolin, Alcohol, mineral oil | 2.00 |
| Cetyl Acetate, acetylated Lanolin alcohol | 2.00 |
| *Murumuru* butter | 3.00 |
| Butylparabene, Ethylparabene, Methylparabene, Phenoxyethanol, Propylparabene | .50 |
| PHASE B | |
| Distilled water qsp | 100.00 |
| Disodium edetate 99.3% | 0.10 |
| FORMULA 4: Reference 01.043 | |
| Creamy Emulsion - Vehicle | |
| PHASE A | |
| Non-ionic self-emulsifying base | 5.00 |
| Keto-stearic alcohol | 2.00 |
| Lanolin, Alcohol, mineral oil | 2.00 |
| Cetyl Acetate, acetylated lanolin alcohol | 2.00 |
| Butylparabene, Ethylparabene, Methylparabene, Phenoxyethanol, Propylparabene | .50 |

-continued

|  | (% pp) |
|---|---|
| PHASE B | |
| Distilled water qsp | 100.00 |
| Disodium edetate 99.3% | 0.10 |

Equivalents

The present invention encompasses many equivalents not specifically disclosed herein. Such equivalents are intended to be encompassed within the scope of the following claims.

The invention claimed is:

1. A method for increasing dermal or capillary hydration of skin comprising applying to skin a composition comprising a dermal or capillary hydrating amount of a natural fat obtained from fruit of a palm tree belonging to the genus *Astrocaryum* and a cream or lotion cosmetic vehicle.

2. The method of claim 1 wherein the fat is extracted from the fruit of one or more species of the palm tree belonging to genus *Astrocaryum*.

3. The method of claim 1 wherein the fat is applied either in its natural state or after purification.

4. The method of claim 1 wherein the fat is obtained from the fruit of a single species of the palm tree belonging to the genus *Astrocaryum*.

5. The method of claim 1 wherein the fat is obtained from a mixture of the fruits from two or more species of the palm tree belonging to the genus *Astrocaryum*.

6. the method of claim 1 wherein the palm tree belonging to the genus *Astrocaryum* is *Astrocaryum murumuru*.

7. The method of claim 1 wherein the cream or lotion cosmetic vehicle comprises a material selected from the group consisting of surfactants, lanolin, mineral oil, fatty acids and fatty acid alcohols.

8. The method of claim 1 wherein the palm tree belonging to the genus *Astrocaryum* is *Astrocaryum tucumã*.

9. The method of claim 1 wherein the palm tree belonging to the genus *Astrocaryum* is *Astrocaryum aculeatum, Astrocaryum awarra, Astrocaryum chambira, Astrocaryum chonta, Astrocaryum faranae, Astrocaryum ferrugineum, Astrocaryum jauari, Astrocaryum macrocalyx, Astrocaryum murumuru, Astrocaryum tucumd, Astrocaryuin ulei or Astrocaryum vulgare*.

10. The method of claim 1 wherein the palm tree belonging to the genus *Astrocaryum* is *Astrocaryum Vulgare, Astrocaryum Chambira, Astrocaryum Juari* or *Astocaryum macrocalyx*.

* * * * *